US011044896B2

(12) United States Patent
Brown et al.

(10) Patent No.: US 11,044,896 B2
(45) Date of Patent: Jun. 29, 2021

(54) T CELL RECEPTORS THAT ARE SPECIFIC TO A FLUORESCENT PROTEIN, TRANSGENIC ANIMALS AND METHODS OF THEIR MAKING, ISOLATED T CELLS, AND METHODS OF USE

(71) Applicant: ICAHN SCHOOL OF MEDICINE AT MOUNT SINAI, New York, NY (US)

(72) Inventors: Brian Brown, New York, NY (US); Judith Agudo, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 15/021,026

(22) PCT Filed: Sep. 12, 2014

(86) PCT No.: PCT/US2014/055492
§ 371 (c)(1),
(2) Date: Mar. 10, 2016

(87) PCT Pub. No.: WO2015/038959
PCT Pub. Date: Mar. 19, 2015

(65) Prior Publication Data
US 2016/0219844 A1    Aug. 4, 2016

Related U.S. Application Data

(60) Provisional application No. 61/877,120, filed on Sep. 12, 2013.

(51) Int. Cl.
| | | |
|---|---|---|
| *A01K 67/027* | (2006.01) | |
| *C07K 14/725* | (2006.01) | |
| *C12N 15/85* | (2006.01) | |
| *G01N 33/566* | (2006.01) | |

(52) U.S. Cl.
CPC ...... *A01K 67/0275* (2013.01); *C07K 14/7051* (2013.01); *C12N 15/8509* (2013.01); *G01N 33/566* (2013.01); *A01K 2217/30* (2013.01); *A01K 2227/105* (2013.01); *A01K 2267/0387* (2013.01); *A01K 2267/0393* (2013.01); *G01N 2333/70503* (2013.01)

(58) Field of Classification Search
CPC ........ A01K 67/0275; A01K 2267/0393; A01K 2217/30; A01K 2227/105; A01K 2267/0387; C12N 15/8509; G01N 33/566; G01N 2333/70503; C07K 14/7051
See application file for complete search history.

(56) References Cited

U.S. PATENT DOCUMENTS

2009/0217403 A1    8/2009   Spits

FOREIGN PATENT DOCUMENTS

| | | |
|---|---|---|
| EP | 1852123 A2 | 7/2007 |
| EP | 1852123 A3 | 10/2008 |
| JP | 2003-518507 A | 6/2003 |
| WO | 91/18019 | 11/1991 |

OTHER PUBLICATIONS

Schleicher et al. "A stable marker for specific T-cells: a TCR alpha/green fluorescent protein (GFP) fusionprotein reconstitutes a functionally active TCR complex." J Immunol Methods. Dec. 1, 2000;246(1-2):165-74.*
Patel et al. "Advances in reprogramming somatic cells to induced pluripotent stem cells." Stem Cell Rev. Sep. 2010;6(3):367-80.*
Hochedlinger and Jaenish. "Nuclear reprogramming and pluripotency." Nature. Jun. 29, 2006;441(7097):1061-7.*
Ogunki et al. "Early death of mice cloned from somatic cells." Nature Genetics 30, 253-254 (2002).*
Hochedlinger et al. "Nuclear transplantation : lessons from frogs and mice" Curr. Opin. Cell Biol. 14, 741-748, 2002.*
Hochedlinger and Jaenish "Monoclonal mice generated by nuclear transfer from mature B and T donor cells" Nature 415, 1035-1038 (Feb. 28, 2002).*
Gambotto et al. "Immunogenicity of enhanced green fluorescent protein (EGFP) in BALB/c mice: identification of an H2-Kd-restricted CTL epitope." Gene Ther. Dec. 2000;7(23):2036-40.*
Murphy and Silha "Unexpected and unexplained phenotypes in transgenic models." Growth Hormone & IGF Research 2000, 10, 233-235.*
Brouwers et al. "Unexpected Phenotypes in Mouse Models Carrying the Human Growth Hormone Minigene to Enhance Transgene Expression." J. Steroids Hormon Sci 2015, 6:1.*
Choi et al. "Expression of the metabotropic glutamate receptor 5 (mGluR5) induces melanoma in transgenic mice." Proc Natl Acad Sci U S A. Sep. 13, 2011; 108(37): 15219-15224.*
Yanta et al. "Unexpected acceleration of type 1 diabetes by transgenic expression of B7-H1 in NOD mouse peri-islet glia." Diabetes. Oct. 2010; 59(10):2588-96.*

(Continued)

*Primary Examiner* — Titilayo Moloye
(74) *Attorney, Agent, or Firm* — Troutman Pepper Hamilton Sanders LLP (Rochester)

(57) ABSTRACT

This invention relates to a transgenic non-human mammal whose genome comprises a polynucleotide sequence encoding a T cell receptor that is specific to a fluorescent protein, where the T cell of the non-human mammal comprises the T cell receptor. The present invention also relates to an isolated T cell from the transgenic non-human mammal of the present invention, an isolated T cell comprising an expression construct comprising a polynucleotide sequence that encodes a T cell receptor that is specific to a fluorescent protein, methods of making transgenic non-human mammals comprising T cell receptors that are specific to a fluorescent protein, a method of depleting cells in a non-human mammal using isolated T cells that encode a T cell receptor that is specific to a target protein, and a method of characterizing a T cell response to an agent.

7 Claims, 7 Drawing Sheets

Specification includes a Sequence Listing.

(56) References Cited

OTHER PUBLICATIONS

Friedman et al. "Real-time analysis of T cell receptors in naive cells in vitro and in vivo reveals flexibility in synapse and signaling dynamics." J Exp Med. Nov. 22, 2010;207(12):2733-49.*
Tomkowiak et al. "Generation of transgenic mice expressing EGFP protein fused to NP68 MHC class I epitope using lentivirus vectors." Genesis. Mar. 2013;51(3):193-200.*
Clarke et al. "Characterization of the ovalbumin-specific TCR transgenic line OT-I: MHC elements for positive and negative selection." Immunol Cell Biol. Apr. 2000;78(2):110-7. (Year: 2000).*
Gambotto et al. "Immunogenicity of enhanced green fluorescent protein (EGFP) in BALB/c mice: identification of an H2-Kd-restricted CTL epitope." Gene Ther. Dec. 2000;7(23):2036-40. (Year: 2002).*
Chudakov et al. "Fluorescent Proteins and Their Applications in Imaging Living Cells and Tissues" Physiol Rev 90: 1103-1163, 2010; (Year: 2010).*
Ansari et al. "Cellular GFP Toxicity and Immunogenicity: Potential Confounders in in Vivo Cell Tracking Experiments." Stem Cell Rev. Oct. 2016;12(5):553-559. (Year: 2016).*
Agudo et al. "GFP-specific CD8 T cells enable targeted cell depletion and visualization of T-cell interactions." Nat Biotechnol. Dec. 2015;33(12):1287-1292 (Year: 2016).*
Mishin et al. "The First Mutant of the Aequorea victoria Green Fluorescent Protein That Forms a Red Chromophore." Biochemistry. Apr. 23, 2008; 47(16): 4666-4673. (Year: 2008).*
Shaner et al. "Advances in fluorescent protein technology." J Cell Sci. Dec. 15, 2007;120(Pt 24):4247-60. (Year: 2007).*
Han et al. "Letter to the Editor Published: Feb. 21, 2008 Identification of the immunodominant CTL epitope of EGFP in C57BL/6 mice" Gene Therapy vol. 15, pp. 700-701(2008) (Year: 2008).*
Rizzo et al. "Fluorescent protein tracking and detection: fluorescent protein structure and color variants." Cold Spring Harb Protoc. Dec. 2009;2009(12):pdb.top63 (Year: 2009).*
EP Search Report for EP Application No. 14843371.7, dated Feb. 3, 2017.
Siliciano et al., "Direct Evidence for the Existence of Nominal Antigen Binding Sites on T Cell Surface Ti α-β Heterodimers of MHC-Restricted T Cell Clones," Cell 47:161-171 (1986).
Park et al., "Treating Cancer With Genetically Engineered T Cells," Trends in Biotechnology, 29(11):550-557 (2011).
Agudo et al., "GFP-specific CD8 T Cells Enable Targeted Cell Depletion and Visualization of T-cell Interactions," Nature Biotechnology 33(12):1287-1292 (2015).
Annoni et al., "In vivo delivery of a microRNA-regulated transgene induces antigen-specific regulatory T cells and promotes immunologic tolerance," Blood 114(25):5152-5161 (2009).
Walchli et al., "A practical approach to T-cell receptor cloning and expression," PLoS One 6(11)(e27930):1-11 (2011).
International Search Report and Written Opinion for corresponding PCT/US2014/055492 (dated Mar. 20, 2015).
Barsov et al., "Transduction of SIV-specific TCR Genes into Rhesus Macaque CD8+ T Cells Conveys the Ability to Suppress SIV Replication," PLOS ONE 6(8):e23703 (2011).
Yui et al., "Self-reactive T cells can escape clonal deletion in T-cell receptor Vbeta8.1 transgenic mice," Proc. Natl. Acad. Sci. USA 87:7135-7139 (1990).
Invitation to Pay Additional Fees from the International Searching Authority, dated Jan. 14, 2015.
Notice of Reasons for Rejection in corresponding Japanese Application No. 2013-542829 dated Aug. 2, 2018.
Hogouist et al., "T Cell Receptor Antagonist Peptides Induce Positive Selection," Cell 76:17-27 (1994).
Gambotto et al., "Immunogenicity of Enhanced Green Fluorescent Protein (EGFP) in BALB/c Mice: Identification of an H2-Kd-Restricted CTL Epitope," Gene Ther. 7(23):2036-2040 (2000).
Stripecke et al., "Immune Response to Green Fluorescent Protein: Implications for Gene Therapy," Gene Ther. 6(7): 1305-1312 (1999).
Partial European Search Report and Search Opinion in corresponding European Patent Application No. 14843371.7, dated Feb. 3, 2017.
Extended EP Search Report in corresponding EP Application No. 14843371.7, dated May 10, 2017.
Communication in corresponding European Patent Application No. 14843371.7 (dated Mar. 29, 2019).
Extended European Search Report and Opinion in corresponding Europe Application No. 19188330.5, dated Nov. 22, 2019.
Examination Report No. 1 in corresponding Australia Application No. 2014318520, dated Sep. 26, 2019.
Intention to Grant in corresponding Europe Application No. 14843371. 7, dated Mar. 29, 2019.
Decision of Reasons for Rejection in corresponding Japan Application No. 2016-542829, dated Jul. 22, 2019.
NCBI Taxonomy Database entries for GenBank Accession No. BD136947.
NCBI Taxonomy Database entries for GenBank Accession No. BD136948.
NCBI Taxonomy Database entries for GenBank Accession No. BD136949.
Notice of Reasons for Rejection in Japan Patent Application No. 2016-542829, dated Nov. 5, 2020 (English Translation).
Office Action for Canadian Application No. 2,922,561 dated Jul. 21, 2020.
Notice of Reasons for Rejection in Japan Patent Application No. 2019-211002, dated Feb. 1, 2021 (English Translation).

* cited by examiner

```
agatggtgga gagtcactgt tgtgattgct agcaaagctg cttttatgt ttcctatagg   60
agatgtgaaa acttatgaac acaactatat gagtttagga ttgagaatct aaatccacag  120
tgaagaggga agaggagaga atgaaatcct tgagtgtttc actagtggtc ctgtggctcc  180
aggtaaactg cgtgaggagc cagcagaagg tgcagcagag cccagaatcc ctcagtgtcc  240
cagagggagg catggcctct ttcaactgca cttcaagtga tcgtaatttt cagtacttct  300
ggtggtacag acagcattct ggagaaggcc caaggcact  gatgtcaatc ttctctgatg  360
gtgacaagaa agaaggcaga ttcacagctc acctcaataa ggccagcctg catgtttccc  420
tgcacatcag agactcccag cccagtgact ccgctctcta cttctgtgca gctagtcatg  480
acacaaatgc ttacaaagtc atctttggaa aagggacaca tcttcatgtt ctccctaaca  540
tccagaaccc agaacctgct gtgtaccagt taaaagatcc tcggtctcag gacagcaccc  600
tctgcctgtt caccgacttt gactcccaaa tcaatgtgcc gaaaaccatg gaatctggaa  660
cgttcatcac tgacaaaact gtgctggaca tgaaagctat ggattccaag agcaatgggg  720
ccattgcctg gagcaaccag acaagcttca cctgccaaga tatcttcaaa gagaccaacg  780
ccacctaccc cagttcagac gttccctgtg atgccacgtt gactgagaaa gctttgaaa   840
cagatatgaa cctaaacttt caaaacctgt cagttatggg actccgaatc ctcctgctga  900
aagtagccgg atttaacctg ctcatgacgc tgaggctgtg gtccagttga ggtctgcaag  960
actgacagag cctgactccc aagctccatc ctcctcaccc ctccgctcct tcttcaagcc 1020
aaaaggagcc ctcccacctc gtcaagacgg ctgtctgggg tctggttggc cctgattcac 1080
aatcccacct ggatctccca gatttgtgag gaaggttgct ggagagctaa gcactgctgc 1140
cgcacccact cagctccctc actgctgctg accattcaca aaaaacggca ggggcggggc 1200
ttctcctgga tctgaagacc cctcccccat ggcagactcc cctgtaaaat ctcttggaga 1260
atgttgtaaa aaaatatcg gttgtttttt gtttttttt ttttgcggg tttatttttt     1320
taagcatcca tgaagaaatg catattactc tttcatcaag gtgtagaaat tatctcattg 1380
tctagaccct cctgctactg tgtgtattga gccacattgt atattattct gctgtccatg 1440
acatcattaa aggtgattca gaaa                                        1464
```

*FIG. 2*

```
Met Lys Ser Leu Ser Val Ser Leu Val Val Leu Trp Leu Gln Val Asn
1               5                   10                  15
Cys Val Arg Ser Gln Gln Lys Val Gln Gln Ser Pro Glu Ser Leu Ser
            20                  25                  30
Val Pro Glu Gly Gly Met Ala Ser Phe Asn Cys Thr Ser Ser Asp Arg
            35                  40                  45
Asn Phe Gln Tyr Phe Trp Trp Tyr Arg Gln His Ser Gly Glu Gly Pro
        50                  55                  60
Lys Ala Leu Met Ser Ile Phe Ser Asp Gly Asp Lys Lys Glu Gly Arg
65                  70                  75                  80
Phe Thr Ala His Leu Asn Lys Ala Ser Leu His Val Ser Leu His Ile
                85                  90                  95
Arg Asp Ser Gln Pro Ser Asp Ser Ala Leu Tyr Phe Cys Ala Ala Ser
            100                 105                 110
His Asp Thr Asn Ala Tyr Lys Val Ile Phe Gly Lys Gly Thr His Leu
            115                 120                 125
His Val Leu Pro Asn Ile Gln Asn Pro Glu Pro Ala Val Tyr Gln Leu
            130                 135                 140
Lys Asp Pro Arg Ser Gln Asp Ser Thr Leu Cys Leu Phe Thr Asp Phe
145                 150                 155                 160
Asp Ser Gln Ile Asn Val Pro Lys Thr Met Glu Ser Gly Thr Phe Ile
            165                 170                 175
Thr Asp Lys Thr Val Leu Asp Met Lys Ala Met Asp Ser Lys Ser Asn
            180                 185                 190
Gly Ala Ile Ala Trp Ser Asn Gln Thr Ser Phe Thr Cys Gln Asp Ile
            195                 200                 205
Phe Lys Glu Thr Asn Ala Thr Tyr Pro Ser Ser Asp Val Pro Cys Asp
            210                 215                 220
Ala Thr Leu Thr Glu Lys Ser Phe Glu Thr Asp Met Asn Leu Asn Phe
225                 230                 235                 240
Gln Asn Leu Ser Val Met Gly Leu Arg Ile Leu Leu Leu Lys Val Ala
                245                 250                 255
Gly Phe Asn Leu Leu Met Thr Leu Arg Leu Trp Ser Ser
            260                 265
```

*FIG. 3*

```
atgggctcca ttttcctcag ttgcctggcc gtttgtctcc tggtggcagg tccagtcgac  60
ccgaaaatta tccagaaacc aaaatatctg gtggcagtca cagggagcga aaaaatcctg 120
atatgcgaac agtatctagg ccacaatgct atgtattggt atagacaaag tgctaagaag 180
cctctagagt tcatgttttc ctacagctat caaaaactta tggacaatca gactgcctca 240
agtcgcttcc aacctcaaag ttcaaagaaa aaccatttag accttcagat cacagctcta 300
aagcctgatg actcggccac atacttctgt gccagcagcc aagggcagg gatctataat 360
tcgcccctct actttgcggc aggcacccgg ctcactgtga cagaggatct gagaaatgtg 420
actccaccca aggtctcctt gtttgagcca tcaaaagcag agattgcaaa caaacaaaag 480
gctaccctcg tgtgcttggc caggggcttc ttccctgacc acgtggagct gagctggtgg 540
gtgaatggca aggaggtcca cagtggggtc agcacggacc ctcaggccta caaggagagc 600
aattatagct actgcctgag cagccgcctg agggtctctg ctaccttctg gcacaatcct 660
cgcaaccact tccgctgcca agtgcagttc catgggcttt cagaggagga caagtggcca 720
gagggctcac ccaaacctgt cacacagaac atcagtgcag aggcctgggg ccgagcagac 780
tgtgggatta cctcagcatc ctatcaacaa ggggtcttgt ctgccaccat cctctatgag 840
atcctgctag ggaaagccac cctgtatgct gtgcttgtca gtacactggt ggtgatggct 900
atggtcaaaa gaaagaattc atga                                        924
```

FIG. 4

```
Met Gly Ser Ile Phe Leu Ser Cys Leu Ala Val Cys Leu Leu Val Ala
1               5                   10                  15
Gly Pro Val Asp Pro Lys Ile Ile Gln Lys Pro Lys Tyr Leu Val Ala
            20                  25                  30
Val Thr Gly Ser Glu Lys Ile Leu Ile Cys Glu Gln Tyr Leu Gly His
            35                  40                  45
Asn Ala Met Tyr Trp Tyr Arg Gln Ser Ala Lys Lys Pro Leu Glu Phe
        50                  55                  60
Met Phe Ser Tyr Ser Tyr Gln Lys Leu Met Asp Asn Gln Thr Ala Ser
65                  70                  75                  80
Ser Arg Phe Gln Pro Gln Ser Ser Lys Lys Asn His Leu Asp Leu Gln
            85                  90                  95
Ile Thr Ala Leu Lys Pro Asp Asp Ser Ala Thr Tyr Phe Cys Ala Ser
            100                 105                 110
Ser Gln Gly Ala Gly Ile Tyr Asn Ser Pro Leu Tyr Phe Ala Ala Gly
            115                 120                 125
Thr Arg Leu Thr Val Thr Glu Asp Leu Arg Asn Val Thr Pro Pro Lys
            130                 135                 140
Val Ser Leu Phe Glu Pro Ser Lys Ala Glu Ile Ala Asn Lys Gln Lys
145                 150                 155                 160
Ala Thr Leu Val Cys Leu Ala Arg Gly Phe Phe Pro Asp His Val Glu
            165                 170                 175
Leu Ser Trp Trp Val Asn Gly Lys Glu Val His Ser Gly Val Ser Thr
            180                 185                 190
Asp Pro Gln Ala Tyr Lys Glu Ser Asn Tyr Ser Tyr Cys Leu Ser Ser
            195                 200                 205
Arg Leu Arg Val Ser Ala Thr Phe Trp His Asn Pro Arg Asn His Phe
            210                 215                 220
Arg Cys Gln Val Gln Phe His Gly Leu Ser Glu Glu Asp Lys Trp Pro
225                 230                 235                 240
Glu Gly Ser Pro Lys Pro Val Thr Gln Asn Ile Ser Ala Glu Ala Trp
            245                 250                 255
```

FIG. 5A

```
Gly Arg Ala Asp Cys Gly Ile Thr Ser Ala Ser Tyr Gln Gln Gly Val
            260                 265                 270
Leu Ser Ala Thr Ile Leu Tyr Glu Ile Leu Leu Gly Lys Ala Thr Leu
            275                 280                 285
Tyr Ala Val Leu Val Ser Thr Leu Val Val Met Ala Met Val Lys Arg
            290                 295                 300
Lys Asn Ser
305
```
FIG. 5B
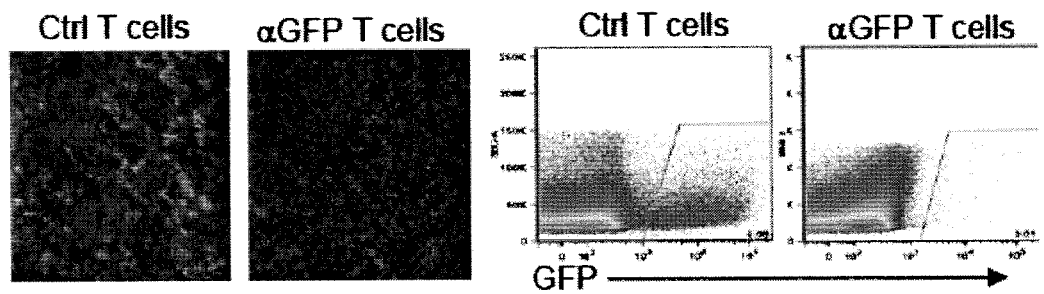
FIG. 6A
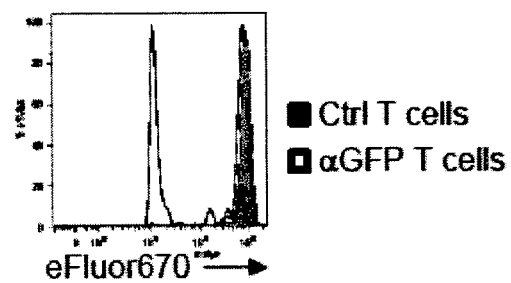
FIG. 6B

T CELL RECEPTORS THAT ARE SPECIFIC TO A FLUORESCENT PROTEIN, TRANSGENIC ANIMALS AND METHODS OF THEIR MAKING, ISOLATED T CELLS, AND METHODS OF USE

This application is a national stage application under 35 U.S.C. § 371 of PCT Application No. PCT/US2014/055492, filed Sep. 12, 2014, which claims the priority benefit of U.S. Provisional Patent Application Ser. No. 61/877,120, filed Sep. 12, 2013, the disclosure of which is incorporated herein by reference in its entirety.

This invention was made with government support under grant number DK083052 awarded by the National Institutes of Health. The government has certain rights in the invention.

FIELD OF THE INVENTION

The present invention relates to T cell receptors that are specific to a fluorescent protein, transgenic animals and methods of their making, isolated T cells, and methods of their use.

BACKGROUND OF THE INVENTION

The adaptive immune system of vertebrates defends the host against infection. T cells play the role of central organizer of the immune response by recognizing antigens through T cell receptors ("TCR"). The specificity of a T cell depends on the sequence of its TCR. The genetic template for this receptor is created during T cell development in the thymus by the V(D)J DNA rearrangement process, which imparts a unique antigen specificity upon each TCR. The TCR plays an essential role in T cell function, development, and survival. Genetic lesions that interfere with the generation of antigen receptors block T cell development and result in immunodeficiencies. Because of the importance of T cells in organizing the immune response, it is desirable to be able to generate T cells having a particular antigen specificity.

One of the ways to study the immune response to a virus or self-antigen is through the use of TCR transgenic mice (TCR-Tg) (Bluthmann et al., "T-cell-specific Deletion of T-cell Receptor Transgenes Allows Functional Rearrangement of Endogenous Alpha- and Beta-genes," *Nature* 334: 156-9 (1988); Lafaille, "T-cell Receptor Transgenic Mice in the Study of Autoimmune Diseases," *Journal of Autoimmunity* 22:95-106 (2004)). These mice are made so that the every T cell in the mouse expresses a single TCR, which recognizes a single antigen. At least 30 different TCR-Tg mice have been made. The antigens recognized by the T cells from the various TCR-Tg mice are peptides derived from proteins expressed by a pathogen, such as the influenza virus, or a peptide derived from a self-protein that is implicated in autoimmune disease, such as myelin basic protein (MBP). This enables the TCR-Tg T cells to be used to study an immune response to a pathogen or to model an autoimmune disease.

The most commonly used antigen-specific TCR mice recognize an epitope from chicken ovalbumin (OVA). Specifically, OT-I and OT-II mice recognize an epitope of OVA presented by MHC class I and MHC class II, respectively. These mice have been used to study T cell responses and to model autoimmune disease.

Though TCR-Tg mice are an invaluable resource for studying particular aspects of immunology, there are several key limitations to all of the existing TCR-Tg models which preclude their use for particular types of applications. Specifically, none of the existing TCR-Tg mice can be used to study the immune response against an antigen that can be visualized by flow cytometry, florescent microscopy, or live cell imaging.

The generation of a GFP-specific T cell ($\alpha$GFP) mouse would address a major deficit in the immunologist's tool box by providing an antigen-specific T cell model that targets a commonly used, easily monitored, florescent reporter. Green fluorescent protein ("GFP") is an ideal model antigen since it is intracellular, can be easily detected, even at single cell resolution and by live cell imaging, and more than 1,000 different transgenic mice have been generated in which GFP is expressed in specific tissues, cell types, or cell states (Schmidt et al., "BAC Transgenic Mice and the GENSAT Database of Engineered Mouse Strains," *Cold Spring Harbor Protocols* (2013)). Plus, there are dozens of cancer cell lines, viruses, and other pathogens that have been engineered to express GFP. The abundance of GFP-based reagents and animal models makes the $\alpha$GFP mouse immediately relevant for scores of labs doing a wide variety of research from trying to understand the antigen presenting capacity of specific cell types to virologists characterizing host-pathogen interactions.

The present invention is directed to overcoming these and other deficiencies in the art.

SUMMARY OF THE INVENTION

A first aspect of the present invention relates to a transgenic non-human mammal whose genome comprises a polynucleotide sequence encoding a T cell receptor that is specific to a fluorescent protein, where a T cell of the non-human mammal comprises the T cell receptor.

A second aspect of the present invention relates to an isolated T cell from the transgenic non-human mammal of the present invention.

A third aspect of the present invention relates to an isolated T cell comprising an expression construct comprising a polynucleotide sequence that encodes a T cell receptor that is specific to a fluorescent protein.

A fourth aspect of the present invention relates to a method of making a transgenic non-human mammal. This method involves introducing an expression construct into a non-human mammalian embryo to produce a transgenic embryo, said expression construct comprising a polynucleotide sequence encoding a T cell receptor that is specific to a fluorescent protein in operable linkage with a promoter; transplanting the transgenic embryo into a pseudopregnant non-human mammal; allowing the transgenic embryo to develop to term; and isolating at least one transgenic offspring containing the polynucleotide.

A fifth aspect of the present invention relates to a method of making a non-human mammal. This method involves providing a non-human mammalian somatic cell or cell nucleus comprising a polynucleotide sequence encoding a T cell receptor that is specific to a fluorescent protein in operable linkage with a promoter; inserting the non-human mammalian somatic cell or cell nucleus into an enucleated oocyte under conditions suitable for the formation of a reconstituted cell; activating the reconstituted cell to form an embryo; culturing the embryo until greater than the 2-cell developmental stage; and transferring the cultured embryo to a host mammal such that the embryo develops into a chimeric fetus capable of growing to a non-human mammal.

A sixth aspect of the present invention relates to a method of depleting cells in a non-human mammal. This method involves providing a non-human mammal that expresses a target protein in one or more cell types and introducing into the non-human mammal an isolated T cell comprising an expression construct comprising a polynucleotide sequence that encodes a T cell receptor that is specific to the target protein, where the isolated T cell attacks the one or more cell types to deplete the one or more cell types in the non-human mammal.

A seventh aspect of the present invention relates to a method of characterizing a T cell response to an agent. This method involves providing a transgenic non-human mammal according to the present invention; introducing into the transgenic non-human mammal an agent selected from the group consisting of a vaccine, a virus, a pathogen, a transplanted cell, and a cancer cell line, where the agent comprises a fluorescent protein and/or a fluorescent protein encoding sequence; and monitoring the interaction between the T cell receptor that is specific to a fluorescent protein and the agent to characterize the T cell response in the transgenic non-human mammal.

The present invention overcomes the limitations of existing TCR-Tg mice, and is directed to a new antigen-specific TCR model. Specifically, GFP-specific TCR mice have been generated that recognize green florescent protein. Accordingly, the present invention is useful for optimizing vaccines used for treating or preventing infectious diseases and cancers, or for inducing immune tolerance. Uniquely, the present invention allows the study the T cell response to the plethora of vaccines, viruses, and cancer cell lines that encode GFP and other fluorescent proteins.

In addition, the present invention provides a way to model autoimmune diseases in tissues and organs in a manner not previously possible. For example, the present invention takes advantage of the hundreds of available varieties of mice that express GFP and other fluorescent proteins specifically in particular cell types or tissues. Transgenic non-human mammals of the present invention can be used to study how T cells respond to antigen presented by these cell types.

Further, the present invention makes it possible to characterize the T cell response to different cancers and metastasis using GFP-expressing tumor cells.

Moreover, the present invention provides a novel method for depleting desired cells in mice to study the function of the cells. GFP-specific T cells can be infused into mice that express GFP in a particular cell type, and these T cells will specifically kill those cells. By depleting these cells, this method provides a "loss-of-function" phenotype which can be studied to understand the role of the cognate cells.

In addition, the present invention makes it possible to perform live cell imaging and intravital microscopy analysis of antigen-specific T cell-mediated killing of a particular cell type, including viral infected cells.

The transgenic non-human mammal of the present invention is the first antigen-specific TCR mouse in which the T cells recognize an epitope of a fluorescent protein. The transgenic non-human mammal of the present invention can be used for studying the immune response to fluorescent proteins, and thereby take advantage of the thousands of GFP (and other fluorescent protein) transgenic mice, GFP (and other fluorescent protein) expressing tumor cell lines, and GFP (and other fluorescent protein) expressing pathogens, to study the immune response in contexts not previously possible. In another application of the technology of the present invention, the transgenic non-human mammals of the present invention can be used as a method to deplete rare cell types in non-human mammals.

BRIEF DESCRIPTION OF THE DRAWINGS

FIG. 2 is the cDNA sequence (SEQ ID NO:1) of the GFP-specific T cell receptor alpha chain in mouse. Nucleotides 1-476 of SEQ ID NO:1 are the trav7-4 domain, nucleotides 479-537 of SEQ ID NO:1 are the traj30 domain, and nucleotides 477-478 are a hypervariable region. Nucleotides 141-950 of SEQ ID NO:1 are the coding region.

FIG. 3 is the amino acid sequence (SEQ ID NO:2) of a GFP-specific T cell receptor alpha chain in mouse.

FIG. 4 is the cDNA sequence (SEQ ID NO:3) of a GFP-specific T cell receptor beta chain in mouse. Nucleotides 1-343 of SEQ ID NO:3 are the trbv2 (Vb4) domain, nucleotides 354-403 of SEQ ID NO:3 are the Trbj1.6 domain, nucleotides 404-924 of SEQ ID NO:3 are the Trbc1 domain, and nucleotides 344-353 are a hypervariable region. Nucleotides 1-924 of SEQ ID NO:3 are the coding region.

FIGS. 5A-B are the amino acid sequence (SEQ ID NO:4) of the GFP-specific T cell receptor beta chain in mouse.

FIGS. 6A-B show that transfer of αGFP T cells rapidly kill GFP expressing splenocytes. eFluor670-labelled αGFP CD8+ of Control T cells were transferred into mice expressing GFP in a subset of splenocytes. As shown in FIG. 6A, after 5 days, the spleen was analyzed for GFP by fluorescence microscopy (right panel) and by FACS (left panel). FIG. 6B shows that T cell proliferation was measured by FACS analysis of eFluor670 dilution. Note that only αGFP T cell proliferated upon adoptive transfer.

In FIG. 7A, blood glucose levels were measured prior to T cell injection and 6 days after injection. All the mice that received αGFP T cells were diabetic based on having glucose levels >250 mg/dl. In FIG. 7B, after 6 days, the pancreas was collected from the mice, and the presence of β cells was assessed by routine histology and by fluorescence microscopy using GFP to score β cells. The mice were also stained for CD8+ T cells and for nuclei using DAPI. Images are representative of 4 mice per group. In MIP-GFP mice that received αGFP T cells, no GFP-positive cells were detected in the pancreas.

DETAILED DESCRIPTION OF THE INVENTION

Figure 1:
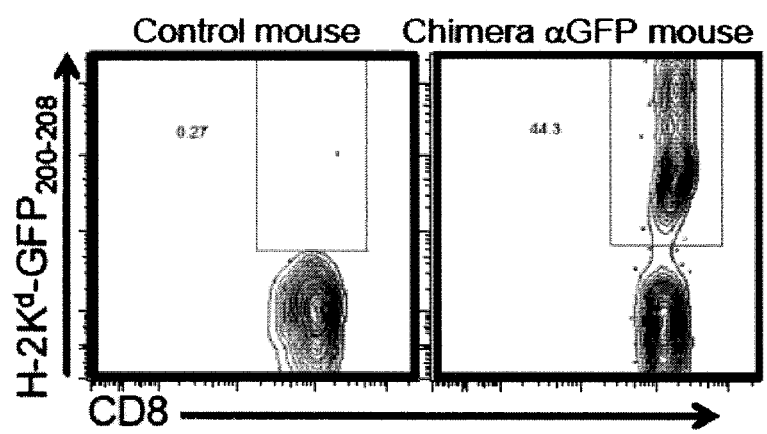
FIG. 1 is a pair of graphs showing detection of GFP-specific CD8+ T cells in founder αGFP mice generated by somatic cell nuclear transfer ("SCNT"). Cells were collected from the lymph nodes of founder αGFP mice. The cells were stained for CD8 and an anti-H-2K$^d$-GFP$_{200-208}$ pentamer. Representative FACS is shown in all 14 founders. Note that these are founder mice and thus chimeric.

The present invention relates to a transgenic non-human mammal whose genome comprises a polynucleotide sequence encoding a T cell receptor that is specific to a fluorescent protein, wherein a T cell of the non-human mammal comprises the T cell receptor.

According to one embodiment, the transgenic non-human mammal of the present invention is a rodent, such as a mouse or a rat. Transgenic non-human mammals may include other species of mammals. For example, transgenic procedures have been successfully utilized in a variety of non-murine mammals, including sheep, goats, pigs, dogs, cats, monkeys, chimpanzees, hamsters, rabbits, cows, and guinea pigs (see, e.g., Kim et al., "Development of a Positive Method for Male Stem-cell Mediated Gene-transfer in Mouse and Pig," *Mol. Reprod. Dev.* 46(4): 515-526 (1997); Houdebine, "The Production of Pharmaceutical Proteins from the Milk of Transgenic Animals," *Reprod. Nutr. Dev.* 35(6):609-617 (1995); Petters, "Transgenic Livestock as Genetic Models of Human Disease," *Reprod. Fertil. Dev.* 6(5):643-645 (1994); Schnieke et al., "Human Factor IX Transgenic Sheep Produced by Transfer of Nuclei from Transfected Fetal Fibroblasts," *Science* 278(5346):2130-2133 (1997); Amoah & Gelaye, "Biotechnology Advances in Goat Reproduction," *J. Animal Science* 75(2):578-585 (1997), which are hereby incorporated by reference in their entirety).

As discussed in more detail infra, transgenic non-human mammals of the present invention can be produced by a variety of different methods including transfection, electroporation, microinjection, gene targeting in embryonic stem cells, and recombinant viral and retroviral infection (see. e.g., U.S. Pat. No. 4,736,866 to Leder et al.; U.S. Pat. No. 5,602,307 to Beaudet et al.; Mullins et al., "Transgenesis in Nonmurine Species," *Hypertension* 22(4):630-633 (1993); Brenin et al., "Transgenic Technology: An Overview of Approaches Useful in Surgical Research," *Surg. Oncol.* 6(2)99-110 (1997); *Methods in Molecular Biology*, vol. 62: Recombinant Gene Expression Protocols, R. Tuan (ed.) Humana Press, Inc., Totowa, N.J. (1997); U.S. Pat. No. 5,489,743 to Robinson et al.; U.S. Pat. No. 5,602,307 to Beaudet et al.; and Lois et al., "Germline Transmission and Tissue-Specific Expression of Transgenes Delivered by Lentiviral Vectors," *Science* 295(5556):868-872 (2002), which are hereby incorporated by reference in their entirety.

According to one embodiment, the transgenic non-human mammal of the present invention comprises a genome that comprises a polynucleotide sequence encoding a T cell receptor that is specific to a fluorescent protein. In other words, the transgenic non-human mammal expresses, through its genome, a polynucleotide sequence encoding a T cell receptor that is specific (e.g., antigen-specific) to a fluorescent protein. Thus, the transgenic non-human mammal comprises lymphocytes that express a desired T cell receptor. The mammal may be produced in such a way that substantially all of the lymphocytes express the desired antigen-specific T cell receptor. Accordingly, the transgenic mammal may be produced by a method comprising contacting a non-human embryonic stem cell with a polynucleotide delivery system that comprises an antigen-specific polynucleotide encoding the desired antigen-specific T cell receptor. In one embodiment, the polynucleotide delivery system comprises a retroviral vector, such as a lentiviral vector.

Alternatively, the transgenic non-human mammal may be produced in such a way that only a sub-population of lymphocytes expresses the desired antigen-specific 'I' cell receptor. According to this embodiment, this sub-population of cells has a unique antigen specificity, and does not express any other antigen-specific polypeptides that are capable of inducing an immune response. In particular, the lymphocytes may not express any other T cell receptors. Such non-human mammals might be produced by contacting hematopoietic stem cells with a polynucleotide delivery system comprising an antigen-specific polynucleotide encoding the desired antigen-specific polypeptide. The hematopoietic stem cells are then transferred into a non-human mammal where they mature into lymphocytes with a unique antigen specificity.

As used herein, the term "specific" as it is used with respect to a T cell receptor that is specific to a fluorescent protein means, according to one embodiment, that the T cell receptor preferentially binds to a fluorescent protein with a higher binding affinity than background interactions between molecules. For example, in the context of the present invention, "background interactions" are interactions with an affinity lower than a $K_D$ of 10E-4 M. Thus, according to one embodiment, a T cell receptor that is specific to a fluorescent protein binds the fluorescent protein with an affinity higher than a $K_D$ of about 10E-5 M.

According to another embodiment, a T cell receptor that is specific to a fluorescent protein means the T cell receptor reacts or associates more frequently, more rapidly, with greater duration, and/or with greater affinity with a fluorescent protein or fluorescent protein expressing cell than it does with non-fluorescent proteins or non-fluorescent protein expressing cells. For example, a T cell receptor that specifically binds to a fluorescent protein binds that fluorescent protein with greater affinity, avidity, more readily, and/or with greater duration than it binds to other non-fluorescent proteins.

T cell receptors that are specific to a fluorescent protein may, according to one embodiment, have the capacity to kill a fluorescent protein expressing cell. In another embodiment, T cell receptors that are specific to a fluorescent protein have the capacity to kill a fluorescent protein expressing cell, and yet lack the capacity to kill a non-fluorescent protein expressing cell.

A T cell receptor that is specific to a fluorescent protein may, according to one embodiment, bind the fluorescent protein at a particular binding site, or epitope, of the fluorescent protein as described herein.

In the transgenic non-human mammal of the present invention, the T cell receptor is specific to either a green fluorescent protein or a yellow fluorescent protein. The fluorescent protein can be a naturally occurring protein or an engineered protein, such as a derivative of the naturally occurring fluorescent proteins. Exemplary fluorescent proteins include, without limitation, *Aequorea*-derived proteins such as GFP, enhanced Green Fluorescent Protein ("eGFP"), and Yellow Fluorescent Protein ("YFP").

Green Fluorescent Protein is a natural fluorescing protein produced by the jellyfish *Aequorea victoria*. Some amino acid residues in the native protein spontaneously form a fluorophore when the polypeptide is folded into an 11-strand beta-barrel threaded by an alpha-helix running up the axis of the internal cylinder. Because it tolerates N- and C-terminal fusion to a broad variety of proteins, GFP has been used primarily as a fluorescent protein tag, i.e., for making chimeric proteins of GFP linked to other proteins where it functions as an indicator to reveal when, where, and how much of the protein it fuses to is present. In this capacity, it has been expressed in bacteria, yeast, slime mold, plants, *Drosophila*, zebrafish, and in mammalian cells.

In the jellyfish from which it was isolated, GFP is involved in physiological interactions with the bioluminescent protein aequorin and shifts its blue light absorption to green light emission through energy transfer. In most applications of GFP, this dual-component configuration is not recapitulated, and the excitation of GFP or its derivatives is afforded through optical instrumentation.

Fluorescent proteins to which the T cell receptor of the transgenic non-human mammal of the present invention is specific include those that contain one or more of the following modifications: circular permutation (Baird et al., "Circular Permutation and Receptor Insertion Within Green Fluorescent Proteins," *Proc. Natl. Acad. Sci. USA* 96:11241-11246 (1999), which is hereby incorporated by reference in its entirety), splitting (Zhang et al., "Combinatorial Marking of Cells and Organelles with Reconstituted Fluorescent Proteins," *Cell* 119:137-144 (2004), which is hereby incorporated by reference in its entirety), enhanced folding (Pedelacq et al., "Engineering and Characterization of a Superfolder Green Fluorescent Protein," *Nat. Biotechnol.* 24:79-88 (2006), which is hereby incorporated by reference in its entirety), or other modifications (Zhang et al., "Creating New Fluorescent Probes for Cell Biology," *Nat. Rev. Mol. Cell Biol.* 3:906-918 (2002), which is hereby incorporated by reference in its entirety).

Specific non-limiting examples of fluorescent proteins (and their encoding nucleic acids) suitable for the present invention include, without limitation, those reported as GenBank Accession Nos. AB195239, AY013821, AY013824, AY013825, AY013826, AY013827, AF435427, AF435428, AF435429, AF435430, AF435431, AF435433, DQ525025, X83959, X83960, X96418, BD136947, BD136948, BD136949, U73901, AF302837, AF183395, AF058694, U50963, L29345, M62653, and M62654.

In one embodiment, the fluorescent protein is a fluorescent protein that comprises the amino acid domain
HYLSTQSAL (SEQ ID NO:5).

In another embodiment, the polynucleotide sequence encoding a T cell receptor that is specific to a fluorescent protein comprises the polynucleotide sequence of SEQ ID NO:1 (FIG. 2), SEQ ID NO:3 (FIG. 4), or a combination of SEQ ID NO:1 and SEQ ID NO:3. The polynucleotide sequences set forth in SEQ ID NO:1 and SEQ ID NO:3 are exemplary. Other polynucleotide sequences encoding a T cell receptor that is specific to a fluorescent protein may also be used. For example, polynucleotide sequences that are similar to and encode antigen-specific T cell receptors may also be used. Such sequences may be at least about 80%, 81%, 82%, 83%, 84%, 85%, 86%, 87%, 88%, 89%, 90%, 91%, 92% 93%, 94%, 95%, 96%, 97%, 98%, or 99% identical SEQ ID NO:1 and SEQ ID NO:3. When using a non-human mammal species other than mouse, the polynucleotide sequence will typically be at least about 80%, 81%, 82%, 83%, 84%, 85%, 86%, 87%, 88%, 89%, 90%, 91%, 92% 93%, 94%, 95%, 96%, 97%, 98%, or 99% identical to the native T cell receptor coding sequence of that species.

As will be appreciated by persons of ordinary skill in the art, within each T cell receptor gene there is a "C region", which codes for a constant domain of the receptor. This region is not directly related to specificity of a fluorescent protein. All the other domains (V regions, J regions, hyper variable region) are variable and it is their specific recombination that provides specificity to a fluorescent protein. Thus, numerous polynucleotide sequences may be designed to generate transgenic non-human mammals whose genome comprises a polynucleotide sequence encoding a T cell receptor that is specific to a fluorescent protein, where a T cell of the non-human mammal comprises the T cell receptor.

In another embodiment, the antigen-specific T cell receptor comprises the amino acid sequence of SEQ ID NO:2 (FIG. 3), SEQ ID NO:4 (FIGS. 5A-B), or a combination of SEQ ID NO:2 and SEQ ID NO:4. The antigen-specific T cell receptor sequences of SEQ ID NO:2 and SEQ ID NO:4 are exemplary, and the present invention is not limited to transgenic non-human mammals containing only these sequences. For example, amino acid sequences that are similar to SEQ ID NO:2 and SEQ ID NO:4 may also be used. Such sequences may be at least about 80%, 81%, 82%, 83%, 84%, 85%, 86%, 87%, 88%, 89%, 90%, 91%, 92% 93%, 94%, 95%, 96%, 97%, 98%, or 99% identical SEQ ID NO:2 and SEQ ID NO:4. Again, when using a non-human mammal species other than mouse, the antigen-specific T cell receptor will typically be at least about 80%, 81%, 82%, 83%, 84%, 85%, 86%, 87%, 88%, 89%, 90%, 91%, 92% 93%, 94%, 95%, 96%, 97%, 98%, or 99% identical to the native T cell receptor of that species.

According to one embodiment, the polynucleotide sequence encoding a T cell receptor is specific to a fluorescent protein loaded into major histocompatibility complex (MHC) I or II.

Another aspect of the present invention relates to an isolated T cell from the transgenic non-human mammal of the present invention.

According to one embodiment, the isolated T cell from the transgenic non-human mammal of the present invention is a purified T cell. Isolated, purified T cells from the transgenic non-human mammals of the present invention can be obtained by several methods known and used by those of ordinary skill in the art. In one embodiment, the isolated T cell is in a purified form (e.g., at least about 80%, 81%, 82%, 83%, 84%, 85%, 86%, 87%, 88%, 89%, 90%, 91%, 92%, 93%, 94%, 95%, 96%, 97%, 98%, or 99% pure).

A further aspect of the present invention relates to an isolated T cell comprising an expression construct comprising a polynucleotide sequence that encodes a T cell receptor that is specific to a fluorescent protein.

Introducing a polynucleotide sequence (i.e., a nucleic acid molecule) encoding a T cell receptor that is specific to a fluorescent protein into an expression system of choice can be carried out using conventional recombinant technology. Generally, this involves inserting the polynucleotide sequence into an expression system to which the molecule is heterologous (i.e., not normally present). The introduction of a particular foreign or native gene into a non-human mammalian host is facilitated by first introducing the gene sequence into a suitable expression construct or vector. "Construct" or "vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression construct or vector in proper sense (5'→3') orientation and correct reading frame. The vector contains the necessary elements for the transcription and translation of the inserted T cell receptor-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see *Stratagene Cloning Systems*

Catalog (1993) from Stratagene, La Jolla, Calif., which is hereby incorporated by reference in its entirety), pQE, pIH821, pGEX, pFastBac series (Invitrogen), pET series (see F. W. Studier et. al., "Use of T7 RNA Polymerase to Direct Expression of Cloned Genes," *Gene Expression Technology*, 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the T cell receptor-encoding sequence in a cell. Primarily, the vector system must be compatible with the host cell used. Host-vector systems include, but are not limited to, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation). Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology* 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the PH promoter, T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno (SD) sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The T cell receptor-encoding nucleic acid, a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., Molecular Cloning: A Laboratory Manual, Third Edition, Cold Spring Harbor Cold Spring Harbor Laboratory Press, New York (2001), which is hereby incorporated by reference in its entirety.

The nucleic acid molecule encoding a T cell receptor that is specific to a fluorescent protein is inserted into a vector in the sense (i.e., 5'→3') direction, such that the open reading frame is properly oriented for the expression of the encoded T cell receptor that is specific to a fluorescent protein under the control of a promoter of choice. Single or multiple nucleic acids may be ligated into an appropriate vector in this way, under the control of a suitable promoter, to prepare a nucleic acid construct.

Once the isolated nucleic acid molecule encoding the T cell receptor that is specific to a fluorescent protein has been inserted into an expression vector, it is ready to be incorporated into a host cell. Recombinant molecules can be introduced into cells via transformation, particularly transduction, conjugation, lipofection, protoplast fusion, mobilization, particle bombardment, or electroporation. The DNA sequences are incorporated into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, non-human mammalian cells, insect cells, plant cells, and the like.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes" which encode enzymes providing for production of an identifiable compound, or other markers which indicate relevant information regarding the outcome of gene delivery, are suitable. For example, various luminescent or phosphorescent reporter genes are also appropriate, such that the presence of the heterologous gene may be ascertained visually.

Another aspect of the present invention relates to a method of making a transgenic non-human mammal. This method involves introducing an expression construct into a non-human mammalian embryo to produce a transgenic embryo, said expression construct comprising a polynucleotide sequence encoding a T cell receptor that is specific to a fluorescent protein in operable linkage with a promoter; transplanting the transgenic embryo into a pseudopregnant non-human mammal; allowing the transgenic embryo to develop to term; and isolating at least one transgenic offspring containing the polynucleotide.

In this method, a polynucleotide sequence encoding a T cell receptor that is specific to a fluorescent protein can be integrated into the genome of the transgenic non-human mammal by any standard method well known to those skilled in the art. Any of a variety of techniques known in the art can be used to introduce the transgene into an animal to produce the founder line of transgenic animals (see e.g., Hogan et al., *Manipulating the Mouse Embryo: A Laboratory Manual*, Cold Spring Harbor Laboratory, 1986; Hogan et al., *Manipulating the Mouse Embryo: A Laboratory Manual*, Cold Spring Harbor Laboratory, 1994; and U.S. Pat. No. 5,602,299 to Lazzarini; U.S. Pat. No. 5,175,384 to Krimpenfort; U.S. Pat. No. 6,066,778 to Ginsburg; and U.S. Pat. No. 6,037,521 to Sato et al, which are hereby incorporated by reference in their entirety). Such techniques include, but are not limited to, pronuclear microinjection (U.S. Pat. No. 4,873,191 to Wagner et al., which is hereby incorporated by reference in its entirety); retrovirus mediated gene transfer into germ lines (Van der Putten et al., *Proc. Natl. Acad. Sci. USA* 82:6148-6152 (1985), which is hereby incorporated by reference in its entirety); gene targeting in embryonic stem cells (Thompson et al., *Cell* 56:313-321 (1989), which is hereby incorporated by reference in its entirety); electroporation of embryos (Lo et al., *Mol. Cell. Biol.* 3:1803-1814 (1983), which is hereby incorporated by reference in its entirety); and sperm-mediated gene transfer (Lavitrano et al., *Cell* 57:717-723 (1989), which is hereby incorporated by reference in its entirety).

For example, embryonic cells at various developmental stages can be used to introduce transgenes for the production of transgenic animals. Different methods are used depending on the stage of development of the embryonic cell. The zygote is a good target for micro-injection, and methods of microinjecting zygote are well known (see U.S. Pat. No. 4,873,191 to Wagner et al., which is hereby incorporated by reference in its entirety). In the mouse, the male pronucleus reaches the size of approximately 20 micrometers in diameter which allows reproducible injection of 1-2 picoliters (pl) of DNA solution. The use of zygotes as a target for gene transfer has an advantage in that in most cases the injected DNA will be incorporated into the host genome before the first cleavage (Brinster et al., *Proc. Natl. Acad. Sci. USA* 82:4438-4442 (1985), which is hereby incorporated by reference in its entirety). As a consequence, all cells of the transgenic non-human animal will carry the incorporated transgene. This will in general also be reflected in the efficient transmission of the transgene to offspring of the founder since 50% of the germ cells will harbor the transgene.

Transgenic animals of the present invention can also be generated by introduction of the targeting vectors into embryonic stem ("ES") cells. ES cells are obtained by culturing pre-implantation embryos in vitro under appropriate conditions (Evans et al., *Nature* 292:154-156 (1981); Bradley et al., *Nature* 309:255-258 (1984); Gossler et al., *Proc. Natl. Acad. Sci. USA* 83:9065-9069 (1986); and Robertson et al., *Nature* 322:445-448 (1986), which are hereby incorporated by reference in their entirety). Transgenes can be efficiently introduced into the ES cells by DNA transfection using a variety of methods known to the art including electroporation, calcium phosphate co-precipitation, protoplast or spheroplast fusion, lipofection and DEAE-dextran-mediated transfection. Transgenes can also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (reviewed in Jaenisch, *Science* 240:1468-1474 (1988), which is hereby incorporated by reference in its entirety). Prior to the introduction of transfected ES cells into the blastocoel, the transfected ES cells can be subjected to various selection protocols to enrich for ES cells that have integrated the transgene if the transgene provides a means for such selection. Alternatively, PCR can be used to screen for ES cells that have integrated the transgene. This technique obviates the need for growth of the transfected ES cells under appropriate selective conditions prior to transfer into the blastocoel.

In addition, retroviral infection can also be used to introduce transgenes into a non-human mammal. The developing non-human embryo can be cultured in vitro to the blastocyst stage. During this time, the blastomeres can be targets for retroviral infection (Janenich, *Proc. Natl. Acad. Sci. USA* 73:1260-1264 (1976), which is hereby incorporated by reference in its entirety). The viral vector system used to introduce the transgene is typically a replication-defective retrovirus carrying the transgene (Jahner et al., *Proc. Natl. Acad. Sci. USA* 82:6927-6931 (1985); Van der Putten et al. *Proc. Natl. Acad. Sci. USA* 82:6148-6152 (1985), which are hereby incorporated by reference in their entirety). Transfection is easily and efficiently obtained by culturing the blastomeres on a monolayer of virus-producing cells. Alternatively, infection can be performed at a later stage. Additional means of using retroviruses or retroviral vectors to create transgenic animals known to the art involves the micro-injection of retroviral particles or mitomycin C-treated cells producing retrovirus into the perivitelline space of fertilized eggs or early embryos (see PCT Publication No. WO 90/08832 to Onions, which is hereby incorporated by reference in its entirety).

The present invention provides transgenic non-human mammals that carry the transgene in all their cells, as well as animals that carry the transgene in some, but not all their cells, i.e., expression of the transgene is controlled by a cell specific promoter and/or enhancer elements placed upstream of the transgene. Expression or cloning constructs suitable for driving transgene expression in a transgenic non-human mammal is well known in the art. Other components of the expression construct include a strong polyadenylation site, appropriate restriction endonuclease sites, and introns to ensure the transcript is spliced.

As discussed supra, the polynucleotide encoding a T cell receptor that is specific to a fluorescent protein can be inserted into any non-human mammal. In one embodiment, the animal is a rodent, for example, a mouse. Suitable strains of mice commonly used in the generation of transgenic models include, without limitation, CD-1® Nude mice, NU/NU mice, BALB/C Nude mice, BALB/C mice, NIH-III mice, SCID® mice, outbred SCID® mice, SCID Beige mice, C3H mice, C57BL/6 mice, DBA/2 mice, FVB mice, CB17 mice, 129 mice, SJL mice, B6C3F1 mice, BDF1 mice, CDF1 mice, CB6F1 mice, CF-1 mice, Swiss Webster mice, SKH1 mice, PGP mice, and B6SJL mice.

The transgenic non-human mammals are screened and evaluated to select those animals having a phenotype, e.g., T cells having T cell receptors that are specific to a fluorescent protein. Initial screening can be performed using fluorescent detection or, for example, Southern blot analysis or PCR techniques to analyze animal cells to verify that integration of the transgene has taken place. The level of mRNA expression of the transgene in the cells of the transgenic animals can also be assessed using techniques which include, but are not limited to, fluorescence detection, Northern blot analysis of tissue samples obtained from the animal, in situ hybridization analysis, and reverse transcriptase-PCR (rt-PCR).

In carrying out this method of the present invention, a transgenic embryo is transplanted into a pseudopregnant non-human mammal. The embryo is the best target for introduction of a transgene by micro-injection. The use of embryos as a target for gene transfer has a major advantage in that in most cases the injected DNA will be incorporated into the host gene before the first cleavage (Brinster et al., "Factors Affecting the Efficiency of Introducing Foreign DNA into Mice by Microinjecting Eggs," *Proc. Nat'l Acad. Sci. USA* 82:4438-4442 (1985), which is hereby incorporated by reference in its entirety). As a consequence, all cells of the transgenic non-human mammal will carry the incorporated transgene. This will, in general, also be reflected in the efficient transmission of the transgene to offspring of the founder since 50% of the germ cells will harbor the transgene.

One means available for producing a transgenic non-human mammal (e.g., a mouse) is as follows: Female mice are mated, and the resulting fertilized eggs are dissected out of their oviducts. The eggs are stored in an appropriate medium such as M2 medium (Hogan et al., "Manipulating the Mouse Embryo, A Laboratory Manual," *Cold Spring Harbor Laboratory* (1986), which is hereby incorporated by reference in its entirety). A DNA or cDNA encoding gene, minigene, or a recombinatorial substrate is purified from a vector (such as plasmids) by methods well known in the art. Inducible promoters may be fused with the coding region of the DNA to provide an experimental means to regulate expression of the transgene. Alternatively, or in addition, tissue specific regulatory elements may be fused with the coding region to permit tissue-specific expression of the transgene. The DNA, in an appropriately buffered solution, is put into a microinjection needle (which may be made from capillary tubing using a pipet puller), and the egg to be injected is put in a depression slide. The needle is inserted into the pronucleus of the egg, and the DNA solution is injected. The injected egg is then transferred into the oviduct of a pseudopregnant non-human mammal (e.g., a mouse stimulated by the appropriate hormones to maintain pregnancy but which is not actually pregnant), where it proceeds to the uterus, implants, and develops to term. This pronuclear DNA microinjection is a classic method for gene transfer and is described by Brem, *Transgenic Animals pp.* 745-832 (1993); and Hammer et al., "Production of Transgenic Rabbits, Sheep and Pigs by Microinjection," *Nature* 315:680-683 (1985), which are hereby incorporated by reference in their entirety. The basic method for DNA microinjection as used in mice is described in Rulicke et al., "Germline Transformation of Mammals by Pronuclear Microinjection," *Experimental Physiology* 85:589-601 (2000), which is hereby incorporated by reference in its entirety. However, some species-specific modifications are necessary in utilizing this method. For example, in the recovery of embryos, the microinjection process and the transfer of injected embryos to the recipients may require modification (Brem, *Transgenic Animals pp.* 745-832 (1993), which is hereby incorporated by reference in its entirety). DNA microinjection is not the only method for inserting DNA into the egg cell, and is used here only for exemplary purposes.

The introducing step of the expression construct may be carried out by several methods well known in the art, which include, but are not limited to, (i) microinjection of genes into the pronuclei of fertilized ova; (ii) DNA transfer by retroviruses; (iii) injection of embryonic stem cells and/or embryonic germ cells, previously exposed to foreign DNA, into the cavity of blastocysts; (iv) sperm mediated exogenous DNA transfer during in vitro fertilization; (v) liposome-mediated DNA transfer into cells and embryos; (vi) electroporation of DNA into sperms, ova, or embryos; (vii) biolistics; and (viii) nuclear transfer with somatic or embryonic cells, which are described in Wheeler et al., "Transgenic Technology and Applications in Swine," *Theriogenology* 56:1345-1370 (2001); Wolf et al., "Transgenic Technology in Farm Animals—Progress and Perspectives," *Exp Physiol.* 85.6:615-625 (2000), which are hereby incorporated by reference in their entirety.

In one embodiment, the nucleic acid construct can be introduced into the embryo by infecting the embryo with a virus containing the nucleic acid construct. A recombinant retrovirus may be used to deliver a transgene of interest to a cell, for example an oocyte or an embryonic cell, or a one-cell embryo. The transgene and any associated genetic elements are thus integrated into the genome of the host cell as a provirus. The cell may then be allowed to develop into a transgenic animal. The developing non-human mammalian embryo can be cultured in vitro to the blastocyst stage. During this time, the blastomeres can be targets for retroviral infection (Jaenich, "Germ Line Integration and Mendelian Transmission of the Exogenous Moloney Leukemia Virus," *Proc Nat'l Acad Sci USA* 73:1260-1264 (1976), which is hereby incorporated by reference in its entirety). Efficient infection of the blastomeres is obtained by enzymatic treatment to remove the zona pellucida (Hogan, et al., *Manipulating the Mouse Embryo* (1986), which is hereby incorporated by reference in its entirety). The viral vector system used to introduce the transgene is typically a replication-defective retrovirus carrying the transgene (Jahner et al., "Insertion of the Bacterial gpt Gene into the Germ Line of Mice by Retroviral Infection," *Proc. Nat'l Acad. Sci. USA* 82:6927-6931 (1985); Van der Putten et al., "Efficient Insertion of Genes into the Mouse Germ Line via Retroviral Vectors," *Proc. Nat'l Acad. Sci. USA* 82:6148-6152 (1985), which are hereby incorporated by reference in their entirety). Transfection is easily and efficiently obtained by culturing the blastomeres on a monolayer of virus-producing cells (Van der Putten et al., "Efficient Insertion of Genes into the Mouse Germ Line via Retroviral Vectors," *Proc. Nat'l Acad. Sci. USA* 82:6148-6152 (1985); Stewart et al., "Expression of Retroviral Vectors in Transgenic Mice Obtained by Embryo Infection," *EMBO J.* 6:383-388 (1987), which are hereby incorporated by reference in their entirety). Alternatively, infection can be performed at a later stage. Virus or virus-producing cells can be injected into the blastocoele (Jahner et al., "De novo Methylation and Expression of Retroviral Genomes during Mouse Embryogenesis," *Nature* 298:623-628 (1982), which is hereby incorporated by reference in its entirety).

In another embodiment, the nucleic acid constructs can be introduced into the embryo by introducing an embryonic stem cell containing the nucleic acid construct into the embryo. Embryonic stem ("ES") cells at various developmental stages can be used to introduce transgenes. Different methods are used depending on the stage of development of the embryonal cell. ES cells may be obtained from pre-implantation embryos cultured in vitro and fused with embryos (Evans et al., "Establishment in Culture of Pluripotential Cells from Mouse Embryos," *Nature* 292:154-156 (1981); Gossler et al., "Transgenesis by Means of Blastocyst-derived Embryonic Stem Cell Lines," *Proc. Nat'l Acad. Sci. USA* 83:9065-9069 (1986), which are hereby incorporated by reference in their entirety). Transgenes can be efficiently introduced into the ES cells by DNA transfection or by retrovirus mediated transduction. Such transformed ES cells can thereafter be combined with blastocysts from a nonhuman mammal. The ES cells thereafter colonize the embryo and contribute to the germ line of the resulting chimeric animal (Jaenisch, "Transgenic Animals," *Science* 240:1468-1474 (1988), which is hereby incorporated by reference in its entirety). For example, one method that can be used is laser-assisted injection of either inbred or hybrid ES cells into eight cell-stage embryos (Poueymirou et al., "F0 Generation Mice Fully Derived from Gene-targeted Embryonic Stem Cells Allowing Immediate Phenotypic Analyses," *Nat. Biotech.* 25:91-99 (2007), which is hereby incorporated by reference in its entirety). This method efficiently yields F0 generation mice that are fully ES cell-derived and healthy, exhibit 100% germline transmission and allow immediate phenotypic analysis, greatly accelerating gene function assignment.

Animals carrying the transgene may be selected by identifying animals which carry a reporter gene contained in the transgenic construct. Such identifying may be carried out by screening for a protein expressed by the gene. For example, by using antibodies specific to the protein which is expressed. The antibodies may also be chemically or radioactively tagged to facilitate detection. The identifying step may also be carried out by screening for a phenotype conferred by the gene (e.g., fluorescence). Such identification may be further carried out by directly screening for the gene, gene product or an RNA molecule made by the gene using nucleic acid hybridization techniques.

In one embodiment, the polynucleotide is expressed in at least a precursor cell of a T cell.

In another embodiment, the precursor cell is a stem cell.

In yet another embodiment, the T cell is a mature T helper cell or mature T cytotoxic cell.

In carrying out this method of the present invention, the embryo is a zygote or a blastomere and the introduction of the polynucleotide into the zygote is carried out by microinjection and introduction of the polynucleotide into the blastomere is by retroviral infection.

A further aspect of the present invention relates to a method of making a non-human mammal. This method involves providing a non-human mammalian somatic cell or cell nucleus comprising a polynucleotide sequence encoding a T cell receptor that is specific to a fluorescent protein in operable linkage with a promoter; inserting the non-human mammalian somatic cell or cell nucleus into an enucleated oocyte under conditions suitable for the formation of a reconstituted cell; activating the reconstituted cell; culturing the embryo until greater than the 2-cell developmental stage; and transferring the cultured embryo to a host mammal such that the embryo develops into a chimeric fetus capable of growing to a non-human mammal.

Somatic cell nuclear transfer for the generation of transgenic non-human mammals is well known (see, e.g., Cibelli et al., "Bovine Chimeric Offspring Produced By Transgenic Embryonic Stem Cells Generated From Somatic Cell Nuclear Transfer Embryos," *Theriogenology* 49:236 (1998); Baguisi et al., "Production of Goats by Somatic Cell Nuclear Transfer," *Nature Biotechnology* 17:456-461 (1999); Polejaeva et al., "New Advances In Somatic Cell Nuclear Transfer: Application In Transgenesis," *Theriogenology* 53:117-126 (2000), which are hereby incorporated by reference in their entirety).

Another aspect of the present invention relates to a method of depleting cells in a non-human mammal. This method involves providing a non-human mammal that expresses a target protein in one or more cell types and introducing into the non-human mammal an isolated T cell comprising an expression construct comprising a polynucleotide sequence that encodes a T cell receptor that is specific to the target protein, where the isolated T cell attacks the one or more cell types to deplete the one or more cell types in the non-human mammal.

In carrying out this method of the present invention, the target protein is, according to one embodiment, a fluorescent protein as described herein, and the polynucleotide sequence encodes a T cell receptor that is antigen specific to the fluorescent protein.

According to one embodiment, in carrying out the method of this aspect of the present invention, the one or more cell types in the non-human mammal are depleted by about 50%, 60%, 70%, 80%, 90%, 95%, 96%, 97%, 98%, 99%, or 100%.

A further aspect of the present invention relates to a method of characterizing a T cell response to an agent. This method involves providing a transgenic non-human mammal according to the present invention; introducing into the transgenic non-human mammal an agent selected from the group consisting of a vaccine, a virus, a pathogen, a transplanted cell, and a cancer cell line, where the agent comprises a fluorescent protein and/or a fluorescent protein encoding sequence; and monitoring the interaction between the T cell receptor that is specific to a fluorescent protein and the agent to characterize the T cell response in the transgenic non-human mammal.

In carrying out this method of the present invention, monitoring of the interaction between the T cell receptor that is specific to a fluorescent protein and the agent can be carried out by detecting the location and concentration of fluorescence, or changes in locations and/or concentrations of fluorescence. Fluorescence can be detected by visual observation. Alternatively, detecting fluorescence may be carried out with a spectrophotometer, or a microscope or macroscope system coupled to a camera or photomultiplier tube. Coupled with proper instrumentation, the optical readout can be followed in real time in living systems to obtain spatio-temporal information (functional intracellular imaging).

These aspects of the present invention are further illustrated by the examples below.

EXAMPLES

The following examples are provided to illustrate embodiments of the present invention but are by no means intended to limit its scope.

Example 1

Generation of an MHC Class I-Restricted GFP-Specific T Cell Receptor (αGFP) Mouse To create a GFP-specific TCR mouse, a somatic cell nuclear transfer (SCNT) approach was used. BALB/c× C57BL/6 F1 (B6CF1) mice were immunized with a DNA vector encoding GFP. By using a BALB/c×C57BL/6 cross, it was possible to induce GFP-specific T cells that recognize GFP on the H-$2K^d$ allele. The H-$2K^d$ allele allows the most diverse use of an antigen-specific TCR mouse since BALB/c mice, NOD mice, and NOD/SCID mice all have the H-$2K^d$ allele, and there are several congenic strains of C57BL/6 mice with the H-$2K^d$ haplotype, most notably B10.D2 mice and B6.D2 mice. This means that any C57BL/6 mouse, including those expressing GFP, can be bred with B10.D2 or B6.D2 mice and all the F1 progeny will have the H-$2K^d$ allele. The immunodominant epitope of GFP presented on H-$2K^d$ is known (GFP$_{200-208}$), and this allows detection of GFP-specific T cells to be determined by tetramer/pentamer staining (FIG. 1).

Two weeks after GFP vaccination, GFP$_{200-208}$-H-$2K^d$pentamer+ CD8+ T cells were FACS sorted from the spleen to >99% purity. SCNT was performed by transferring the nucleus of a GFP-specific T cell to an enucleated oocyte. The ESCs that resulted from the SCNT were expanded, and it was confirmed the cells carried the rearranged TCR. The GFP-TCR ESCs were injected into blastocytes, and the embryos were transferred into pseudopregnant females. Fifteen founder pups were born, and all showed overt evidence of chimerism based on coat color. Subsequent analysis indicated that in every mouse, at least 30% of T cells were specific for the GFP$_{200-208}$-H-$2K^d$pentamer (FIG. 1), and PCR analysis revealed that the rearranged TCR were Vα1-J30 and Vβ4-D141.6-C1 (FIGS. 2-4 provide the cDNA and amino acid sequences of the alpha and beta chains).

Example 2

Transfer of αGFP T Cells into Mice Expressing GFP in the Spleen Induces Killing of GFP+ Splenocytes The GFP-specific killing capacity of the T cells was characterized from the αGFP mice. CD8+ T cells were isolated from αGFP mice or control mice (B10D2), labeled with eFluor670 dye, and transferred to normal B10D2 mice, or mice expressing GFP in a small number of splenocytes. The mice were immunized with GFP, and after 5 days, the spleen were collected and the frequency of GFP+ cells was scored by florescence microscopy and by FACS (FIG. 6A). In mice that received αGFP T cells, GFP+ cells were virtually undetectable indicating that the αGFP T cells killed the GFP expressing splenocytes. Importantly, eFluor670 dye was completely diluted in αGFP T cells that were transferred into the GFP-expressing mice (FIG. 6B), whereas there was no dye dilution when the αGFP T cells were transferred to wildtype mice. There was also no dye dilution from wildtype CD8+ T cells transferred into the GFP-expressing mice. Thus, the data demonstrate that αGFP T cells proliferate in response to GFP presentation, and kill GFP-expressing cells.

Example 3

Figure 7A:
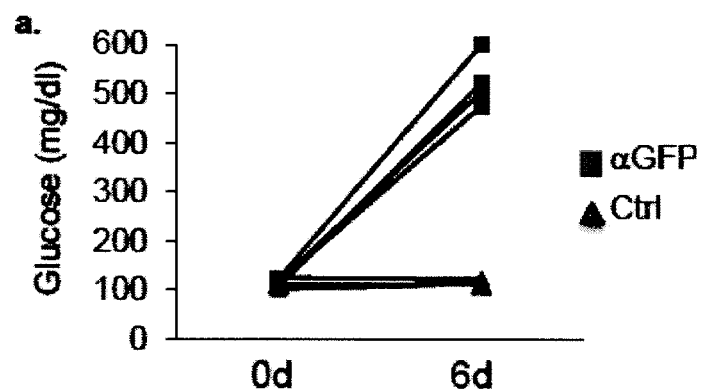
FIGS. 7A-B show that transfer of αGFP CD8+ T cells induces diabetes in mouse insulin promoter GFP (MIP-GFP) mice. 3×10$^6$ T cells were transferred from wildtype mice or αGFP mice into MIP-GFP mice on the B10D2 background (n=4/group).

Transfer of αGFP T Cells into MIP-GFP Mice Induces Killing of GFP-Expressing β Cells and T1D It was next determined if the αGFP T cells could be used to induce β cell killing and diabetes in mice that express GFP specifically in insulin producing β cells (MIP-GFP mice). CD8+ T cells were collected from αGFP mice or B10D2 controls, 3×$10^6$ αGFP T cells were transferred into the MIP-GFP mice, and the following day the mice were immunized against GFP. Strikingly, within 6 days, all 4 mice injected with the GFP-specific T cells had glucose levels >250 mg/dl, indicating a drop in insulin levels (FIG. 7A). Instead, the MIP-GFP mice that received control T cells were all normogycemic in all determinations.

Figure 7B:
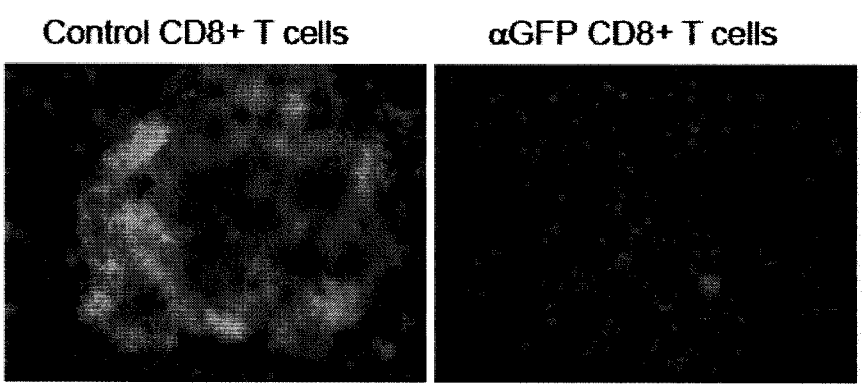

All the mice were sacrificed at 6 days, and β cell mass was assessed by scoring for GFP-positive cells. In mice that received the GFP-specific T cells and were vaccinated with GFP, no GFP-positive cells were found. Whereas, in mice that received the control T cells, no T cell infiltration was seen and the frequency of GFP-expressing islets was comparable to untreated MIP-GFP mice (FIG. 7B). These results clearly demonstrate that αGFP T cells can be transferred into MIP-GFP mice, kill GFP-expressing β cells, and induce diabetes. This represents a new inducible and antigen-specific model of T1D. Of note, this is one of the only models of T1D on the C57BL/6 background and the only model of diabetes where the target islet-antigen can be visualized.

Discussion of Examples 1-3

The first antigen-specific TCR mouse that recognizes a commonly used reporter gene, green florescent protein (GFP), has been invented. Since its initial application as a reporter in *C. elegans* (Chalfie et al., "Green Fluorescent Protein as a Marker for Gene Expression," *Science* 263:802-805 (1994), which is hereby incorporated by reference in its entirety), GFP has found its way into thousands of different applications and animal models, and has become an invaluable technology for immunologists, tumor biologists, and virologists (Chudakov et al., "Fluorescent Proteins and their Applications In Imaging Living Cells and Tissues," *Physiol. Rev.* 90:1103-1163 (2010), which is hereby incorporated by reference in its entirety). However, GFP has not been used as a model immunological antigen. There are many types of studies that will be made possible by the αGFP mice, which were not previously conceivable. Of particular note are: (1) the ability to visualize the antigen, and the elimination of the cell containing the antigen, using florescence imaging technologies (flow cytometry, microscopy, etc.); (2) the ability to utilize existing GFP reagents, which include GFP expressing viruses and GFP mice; (3) the ability to induce an antigen-specific immune response in virtually any cell type to model autoimmune responses; (4) the ability to study immune responses against different GFP expressing pathogens and pathogen mutants; and (5) the ability to visualize the antigen and mark the cells presenting the antigen for live cell imaging studies of antigen-specific T cell responses.

For example, a major question in immunology is how T cells interact with a particular target cell that is presenting its antigen. Because there are hundreds of mouse models that express GFP in different cell types (The Jackson Laboratory (Bar Harbor, Me.) sells more than 400 different GFP expressing strains), one can collect αGFP T cells from mice, and transfer them into one of the GFP-expressing mice, and determine what happens to the T cells (e.g., Do they become activated? Are they deleted or anergized?), and what happens to the cells (Are they killed?). The fact that the target cells express GFP makes the latter particularly easy to assess. With the ability to transfer αGFP cells into many different mice, immunologists will be able to find cells that promote tolerance and immunity, and potentially develop vaccines that target these cells for inducing immunity or tolerance.

In addition to studying immune responses, it is also proposed that the αGFP mice can be used as a means for cell-specific deletion for loss-of-function studies. That is, the αGFP T cells can be transferred into a mouse that expresses GFP in a particular cell type in which the function is not known or not completely known. This will result in killing of the GFP-expressing cells, and the phenotype of the mouse can be assessed to determine the consequence of killing the particular cells.

All of the features described herein (including any accompanying claims, abstract and drawings), and/or all of the steps of any method or process so disclosed, may be combined with any of the above aspects in any combination, except combinations where at least some of such features and/or steps are mutually exclusive.

What is claimed:

1. A transgenic mouse whose genome comprises a transgene encoding a T cell receptor that is specific to a fluorescent protein loaded onto a major histocompatibility complex (MHC) I, wherein the major histocompatibility complex (MHC) I is an H-2K$^d$ MHC I, wherein the fluorescent protein comprises SEQ ID NO:5 and is green fluorescent protein or enhanced green fluorescent protein, wherein a CD8$^+$ T cell of the transgenic mouse comprises the T cell receptor, and wherein the CD8$^+$ T cell is capable of killing a cell expressing the fluorescent protein.

2. The transgenic mouse according to claim 1, wherein the T cell receptor is encoded by a polynucleotide sequence selected from the group consisting of SEQ ID NO:1, SEQ ID NO:3, and both SEQ ID NO:1 and SEQ ID NO:3.

3. The transgenic mouse according to claim 1, wherein the T cell receptor comprises the amino acid sequence selected from the group consisting of SEQ ID NO:2, SEQ ID NO:4, and both SEQ ID NO:2 and SEQ ID NO:4.

4. An isolated T cell from the transgenic mouse of claim 1.

5. A transgenic mouse whose genome comprises a transgene encoding a T cell receptor that is specific to a fluorescent protein loaded onto a major histocompatibility complex (MHC) I, wherein the major histocompatibility complex (MHC) I is an H-2K$^d$ MHC I, wherein the fluorescent protein comprises SEQ ID NO:5 and is green fluorescent protein or enhanced green fluorescent protein, wherein a CD8$^+$ T cell of the transgenic mouse comprises the T cell receptor, wherein the CD8$^+$ T cell is capable of killing a cell expressing the fluorescent protein, and wherein the T cell receptor comprises the amino acid sequence selected from the group consisting of SEQ ID NO:2, SEQ ID NO:4, and both SEQ ID NO:2 and SEQ ID NO:4.

6. The transgenic mouse according to claim 5, wherein the T cell receptor is encoded by a polynucleotide sequence selected from the group consisting of SEQ ID NO:1, SEQ ID NO:3, and both SEQ ID NO:1 and SEQ ID NO:3.

7. An isolated T cell from the transgenic mouse of claim 5.

* * * * *

SEQUENCE LISTING

<160> NUMBER OF SEQ ID NOS: 5

<210> SEQ ID NO 1
<211> LENGTH: 1464
<212> TYPE: DNA
<213> ORGANISM: Mus musculus

<400> SEQUENCE: 1

```
agatggtgga gagtcactgt tgtgattgct agcaaagctg cttttatgt ttcctatagg      60 agatgtgaaa acttatgaac acaactatat gagtttagga ttgagaatct aaatccacag    120
tgaagaggga agaggagaga atgaaatcct tgagtgtttc actagtggtc ctgtggctcc    180
aggtaaactg cgtgaggagc cagcagaagg tgcagcagag cccagaatcc ctcagtgtcc    240
cagagggagg catggcctct ttcaactgca cttcaagtga tcgtaatttt cagtacttct    300
ggtggtacag acagcattct ggagaaggcc ccaaggcact gatgtcaatc ttctctgatg    360
gtgacaagaa agaaggcaga ttcacagctc acctcaataa ggccagcctg catgtttccc    420
tgcacatcag agactcccag cccagtgact ccgctctcta cttctgtgca gctagtcatg    480
acacaaatgc ttacaaagtc atctttggaa aagggacaca tcttcatgtt ctccctaaca    540
tccagaaccc agaacctgct gtgtaccagt taaaagatcc tcggtctcag gacagcaccc    600
tctgcctgtt caccgacttt gactcccaaa tcaatgtgcc gaaaaccatg gaatctggaa    660
cgttcatcac tgacaaaact gtgctggaca tgaaagctat ggattccaag agcaatgggg    720
ccattgcctg gagcaaccag acaagcttca cctgccaaga tatcttcaaa gagaccaacg    780
ccacctaccc cagttcagac gttccctgtg atgccacgtt gactgagaaa agctttgaaa    840
cagatatgaa cctaaacttt caaaacctgt cagttatggg actccgaatc ctcctgctga    900
aagtagccga atttaacctg ctcatgacgc tgaggctgtg gtccagttga ggtctgcaag    960
actgacagag cctgactccc aagctccatc ctcctcaccc ctccgctcct tcttcaagcc   1020
aaaaggagcc ctcccacctc gtcaagacgg ctgtctgggg tctggttggc cctgattcac   1080
aatcccacct ggatctccca gatttgtgag gaaggttgct ggagagctaa gcactgctgc   1140
cgcacccact cagctccctc actgctgctg accattcaca aaaacggca ggggcggggc   1200 ttctcctgga tctgaagacc cctcccccat ggcagactcc cctgtaaaat ctcttggaga   1260
atgttgtaaa aaaaatatcg gttgtttttt gttttttttt ttttgcggg tttatttttt   1320 taagcatcca tgaagaaatg catattactc tttcatcaag gtgtagaaat tatctcattg   1380
```

```
tctagaccct cctgctactg tgtgtattga gccacattgt atattattct gctgtccatg    1440
acatcattaa aggtgattca gaaa                                           1464
```

<210> SEQ ID NO 2
<211> LENGTH: 269
<212> TYPE: PRT
<213> ORGANISM: Mus musculus

<400> SEQUENCE: 2

```
Met Lys Ser Leu Ser Val Ser Leu Val Val Leu Trp Leu Gln Val Asn
1               5                   10                  15

Cys Val Arg Ser Gln Gln Lys Val Gln Gln Ser Pro Glu Ser Leu Ser
            20                  25                  30

Val Pro Glu Gly Gly Met Ala Ser Phe Asn Cys Thr Ser Ser Asp Arg
        35                  40                  45

Asn Phe Gln Tyr Phe Trp Trp Tyr Arg Gln His Ser Gly Glu Gly Pro
    50                  55                  60

Lys Ala Leu Met Ser Ile Phe Ser Asp Gly Asp Lys Lys Glu Gly Arg
65                  70                  75                  80

Phe Thr Ala His Leu Asn Lys Ala Ser Leu His Val Ser Leu His Ile
                85                  90                  95

Arg Asp Ser Gln Pro Ser Asp Ser Ala Leu Tyr Phe Cys Ala Ala Ser
            100                 105                 110

His Asp Thr Asn Ala Tyr Lys Val Ile Phe Gly Lys Gly Thr His Leu
        115                 120                 125

His Val Leu Pro Asn Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 3
<211> LENGTH: 924
<212> TYPE: DNA
<213> ORGANISM: Mus musculus

<400> SEQUENCE: 3

```
atgggctcca ttttcctcag ttgcctggcc gtttgtctcc tggtggcagg tccagtcgac      60
ccgaaaatta tccagaaacc aaaatatctg gtggcagtca cagggagcga aaaatcctg     120 atatgcgaac agtatctagg ccacaatgct atgtattggt atagacaaag tgctaagaag    180
cctctagagt tcatgttttc ctacagctat caaaaactta tggacaatca gactgcctca    240
```

```
agtcgcttcc aacctcaaag ttcaaagaaa aaccatttag accttcagat cacagctcta    300
aagcctgatg actcggccac atacttctgt gccagcagcc aagggcagg gatctataat    360 tcgcccctct actttgcggc aggcacccgg ctcactgtga cagaggatct gagaaatgtg    420
actccaccca aggtctcctt gtttgagcca tcaaaagcag agattgcaaa caaacaaaag    480
gctaccctcg tgtgcttggc agggcttc ttccctgacc acgtggagct gagctggtgg    540
gtgaatggca aggaggtcca cagtggggtc agcacggacc ctcaggccta caaggagagc    600
aattatagct actgcctgag cagccgcctg agggtctctg ctaccttctg gcacaatcct    660
cgcaaccact tccgctgcca agtgcagttc catgggcttt cagaggagga caagtggcca    720
gagggctcac ccaaacctgt cacacagaac atcagtgcag aggcctgggg ccgagcagac    780
tgtgggatta cctcagcatc ctatcaacaa ggggtcttgt ctgccaccat cctctatgag    840
atcctgctag gaaagccac cctgtatgct gtgcttgtca gtacactggt ggtgatggct    900
atggtcaaaa gaaagaattc atga                                           924
```

<210> SEQ ID NO 4
<211> LENGTH: 307
<212> TYPE: PRT
<213> ORGANISM: Mus musculus

<400> SEQUENCE: 4

```
Met Gly Ser Ile Phe Leu Ser Cys Leu Ala Val Cys Leu Leu Val Ala
1               5                   10                  15

Gly Pro Val Asp Pro Lys Ile Ile Gln Lys Pro Lys Tyr Leu Val Ala
            20                  25                  30

Val Thr Gly Ser Glu Lys Ile Leu Ile Cys Glu Gln Tyr Leu Gly His
        35                  40                  45

Asn Ala Met Tyr Trp Tyr Arg Gln Ser Ala Lys Lys Pro Leu Glu Phe
    50                  55                  60

Met Phe Ser Tyr Ser Tyr Gln Lys Leu Met Asp Asn Gln Thr Ala Ser
65                  70                  75                  80

Ser Arg Phe Gln Pro Gln Ser Ser Lys Lys Asn His Leu Asp Leu Gln
                85                  90                  95

Ile Thr Ala Leu Lys Pro Asp Asp Ser Ala Thr Tyr Phe Cys Ala Ser
            100                 105                 110

Ser Gln Gly Ala Gly Ile Tyr Asn Ser Pro Leu Tyr Phe Ala Ala Gly
        115                 120                 125

Thr Arg Leu Thr Val Thr Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255
```

-continued

```
Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
    290                 295                 300

Lys Asn Ser
305

<210> SEQ ID NO 5
<211> LENGTH: 9
<212> TYPE: PRT
<213> ORGANISM: Artificial
<220> FEATURE:
<223> OTHER INFORMATION: Domain of Fluorescent Protein

<400> SEQUENCE: 5

His Tyr Leu Ser Thr Gln Ser Ala Leu
1               5
```